(12) United States Patent
Durocher (10) Patent No.: US 9,085,627 B2
(45) Date of Patent: Jul. 21, 2015

(54) EXPRESSION SYSTEM WITH SAR ELEMENT FROM IFNα2

(75) Inventor: Yves Durocher, Quebec (CA)

(73) Assignee: National Research Council of Canada, Ottawa, Ontario ( * ) Notice: Subject to any disclaimer, the term of this patent is extended or adjusted under 35 U.S.C. 154(b) by 0 days.

(21) Appl. No.: 14/110,944

(22) PCT Filed: Mar. 20, 2012

(86) PCT No.: PCT/CA2012/000254
§ 371 (c)(1),
(2), (4) Date: Oct. 10, 2013

(87) PCT Pub. No.: WO2012/139195
PCT Pub. Date: Oct. 18, 2012

(65) Prior Publication Data
US 2014/0038234 A1    Feb. 6, 2014

Related U.S. Application Data

(60) Provisional application No. 61/474,879, filed on Apr. 13, 2011.

(51) Int. Cl.
| | | |
|---|---|---|
| C12P 21/06 | (2006.01) | |
| C07K 16/28 | (2006.01) | |
| C07K 14/56 | (2006.01) | |
| C12N 15/85 | (2006.01) | |
| C07K 14/575 | (2006.01) | |
| C12N 15/00 | (2006.01) | |
| C07H 21/00 | (2006.01) | |
| C07H 21/02 | (2006.01) | |
| C07H 21/04 | (2006.01) | |

(52) U.S. Cl.
CPC ............. *C07K 16/2863* (2013.01); *C07K 14/56* (2013.01); *C07K 14/575* (2013.01); *C12N 15/85* (2013.01); *C12N 2830/46* (2013.01); *C12N 2830/85* (2013.01)

(58) Field of Classification Search
None
See application file for complete search history.

(56) References Cited

U.S. PATENT DOCUMENTS

| 2005/0170450 A1 | 8/2005 | Durocher |
| 2008/0070232 A1 | 3/2008 | Durocher |
| 2008/0124760 A1 | 5/2008 | Enenkel |

FOREIGN PATENT DOCUMENTS

| CN | 1524875 | 9/2004 |
| WO | WO2005040377 | 5/2005 |
| WO | WO2005040384 | 5/2005 |
| WO | WO2006096989 | 9/2006 |
| WO | WO2008023247 | 2/2008 |
| WO | WO2008116931 | 10/2008 |

OTHER PUBLICATIONS

Kim et al., "Efficient Selection of Stable Chinese Hamster Ovary (CHO) Cell Lines for Expression of Recombinant Proteins by Using Human Interferon β SAR Element" 21 Biotechnology Progress 933-937 (2005).*
Maston et al., "Transcriptional Regulatory Elements in the Human Genome" 7 The Annual Review of Genomics and Human Genetics 29-59 (2006).*
Alvarez JD, et al. (2000) The MAR-binding protein SATB1 orchestrates temporal and spatial expression of multiple genes during T-cell development. Genes & Development. 14(5), 521-35.
Dang Q, Auten J, Plavec I. (2000) Human Beta Interferon Scaffold Attachment Region Inhibits De Novo Methylation and Confers Long-Term, Copy Number-Dependent Expression to a Retroviral Vector. Journal of Virology. 74(6), 2671-2678.
Durocher Y, Perret S, Kamen A. (2002) High-level and high-throughput recombinant protein production by transient transfection of suspension-growing human 293-EBNA1 cells. Nucleic Acids Res. 30(2), E9.
Giannakopoulos A, Stavrou EF, Zarkadis I, Zoumbos N, Thrasher AJ, Athanassiadou A. (2009) The Functional Role of S/MARs in Episomal Vectors as Defined by the Stress-Induced Destabilization Profile of the Vector Sequences. J. Mol. Biol. 387, 1239-1249.
Girod PA, Zahn-Zabal M, Mermod N. (2005) Use of the chicken lysozyme 5' matrix attachment region to generate high producer CHO cell lines. Biotechnology and Bioengineering. 91(1), 1-11.
Girod PA, et al. (2007) Genome-wide prediction of matrix attachment regions that increase gene expression in mammalian cells. Nature Methods. 4(9), 747-53.
Halweg C, Thompson WF, Spiker S. (2005) The rb7 matrix attachment region increases the likelihood and magnitude of transgene expression in tobacco cells: a flow cytometric study. The Plant Cell. 17(2), 418-29.
Jenke AC, et al. (2004) Expression of a transgene encoded on a non-viral episomal vector is not subject to epigenetic silencing by cytosine methylation. Molecular Biology Reports. 31(2), 85-90.
Kim JM, et al. (2004) Improved recombinant gene expression in CHO cells using matrix attachment regions. Journal of Biotechnology. 107(2), 95-105.
Klehr D, Schlake T, Maass K, Bode J. (1992) Scaffold-Attached Regions (SAR Elements) Mediate Transcriptional Effects Due to Butyrate. Biochemistry. 31, 3222-3229.
Liu J, et al. (1997) The matrix attachment region-binding protein SATB1 participates in negative regulation of tissue-specific gene expression. Molecular and Cellular Biology. 17(9), 5275-87.
Lufino MMP, Edser PAH, Wade-Martins R. (2008) Advances in High-capacity Extrachromosomal Vector Technology: Episomal Maintenance, Vector Delivery, and Transgene Expression. Molecular Therapy. 16(9), 1525-1538.

(Continued)

*Primary Examiner* — Celine Qian
*Assistant Examiner* — Nancy J Leith
(74) *Attorney, Agent, or Firm* — Sonia Patenaude (57) ABSTRACT

A short human genomic nucleotide sequence from the SAR3 region of the human interferon α2 gene permits enhances expression stability in the absence of drug selection and permits generation of stable clones or stable pools of cells for producing recombinant proteins. Although stable clones may be generated, the ability to generate stable pools reduces the burden of generating stable clones.

14 Claims, 10 Drawing Sheets

(56) References Cited

OTHER PUBLICATIONS

Phi-Van L, et al. (1990) The chicken lysozyme 5' matrix attachment region increases transcription from a heterologous promoter in heterologous cells and dampens position effects on the expression of transfected genes. Molecular and Cellular Biology. 10(5), 2302-7.

Sass AV, Ruda VM, Akopov SB, Snezhkov EV, Nikolaev LG, Sverdlov ED. (2005) Regulatory Potential of S/MAR Elements in Transient Expression. Russian Journal of Bioorganic Chemistry. 31(1), 70-73.

Strissel PL, Dann HA, Pomykala HM, Diaz MO, Rowley JD, Olopade OI. (1998) Scaffold-Associated Regions in the Human Type I Interferon Gene Cluster on the Short Arm of Chromosome 9. Genomics. 47, 217-229.

Winkelmann S, Klar M, Benham C, Prashanth AK, Goetze S, Gluch A, Bode J. (2006) The positive aspects of stress: strain initiates domain decondensation (SIDD). Briefings in Functional Genomics and Proteomics. 5(1), 24-31.

Zahn-Zabal M, et al. (2001) Development of stable cell lines for production or regulated expression using matrix attachment regions. J. Biotechnol. 87(1), 29-42.

Zhang J, et al. (2009) Transient expression and purification of chimeric heavy chain antibodies. Protein Expr Purif. 65 (1), 77-82.

Brosius J. (2008) The Effect of Putative Chromatin-Opening Element on the Methotrexate Amplification of CHO Cells. A Major Qualifying Project Report Submitted to the Worcester Polytechnic Institute published Jan. 9, 2008.

ISR and WO for PCT/CA2012/000254 mailed Jul. 18, 2012.

European Search Report for corresponding EP Application No. 12771313.9, Nov. 18, 2014.

Office Action issued by Chinese Office Action dated Aug. 28, 2014 for corresponding Chinese Patent Application No. 201280029190.9.

English Translation of Chinese Office Action dated Aug. 28, 2014 for corresponding Chinese Patent Application No. 201280029190.9.

GenBank U82705.1 published Jan. 23, 1997.

English Abstract for CN1524875 published Sep. 1, 2004.

\* cited by examiner

SAR IFNalpha (3483 bps)

Fig. 3A pTT54-EPO
5735 bps

Fig. 3B pTT55-EPO
4985 bps

Erythropoietin dpt: days post-transfection

Pool maintained under puromycin selection

Pool CHO (20 dpt) d5 batch: pTT54, pTT55

Pool CHO (60 dpt) d6 batch: pTT54, pTT55

} hEPO

Anti-hEPO

Fig. 3C

CHO clone (+S/MAR) (days w/o selection)

Ctrl  50

} hEPO (140 mg/L)

Fig. 3D pTT54 (+S/MAR)

|   | 1 | 2 | 3 | 4 | 5 | 6 | 7 | 8 | 9 | 10 | 11 | 12 |
|---|---|---|---|---|---|---|---|---|---|----|----|----|
| A |   |   |   | • |   | • | • |   | • |    | ⊙  |    |
| B |   | • |   | • |   |   |   |   | • | •  | •  | •  |
| C |   |   | • | • | • | • |   |   | • | •  |    | •  |
| D |   | • | • | ⊙ | ⊙ |   | ⊙ | ⊙ |   |    |    |    |
| E |   | • |   |   | ⊙ |   |   |   | • |    |    | •  |
| F | • | • |   |   |   | • | • |   | • | •  |    | •  |
| G |   |   | • | • | • |   |   |   | • | •  |    |    |
| H | • | • | • |   |   |   |   | • | • |    |    | ⊙  | pTT55 (-S/MAR)

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   | • |   |   |    |    |    |
| B |   |   |   |   | • |   |   |   |   |    |    |    |
| C | • |   |   |   |   |   |   |   |   |    |    |    |
| D |   |   |   |   |   |   | ⊙ |   |   |    |    | • |
| E | ⊙ | ⊙ |   |   |   |   |   |   |   |    |    |    |
| F |   | • |   |   |   | • |   |   |   |    | •  |    |
| G |   |   |   |   |   |   |   |   |   |    |    |    |
| H |   |   |   |   |   | • |   |   |   |    |    | ⊙ |

SEQUENCE LISTING

```
<160> NUMBER OF SEQ ID NOS: 1

<210> SEQ ID NO 1
<211> LENGTH: 751
<212> TYPE: DNA
<213> ORGANISM: Homo sapiens

<400> SEQUENCE: 1
aatcagagaa acaaaaatgt tagaaaattc ttgcaggtga ttttcaatat tgttttattt      60
tgtgcaaaaa ataattaacc ttttagaagg tcccagagta ttagaagccc aaactctgga    120
atattctcaa ttttagttga gcttttcagt tattataata ttgtatagct actcataaa     180 ttagtaatac aaaagattct gagtcttatt tgtaaataaa gttcaaaata agtcatatgt    240
tatatgttat aggtaatcat gttagatata aaccactatt gaaaaagata taaaaacaaa    300
ataactttat tttttgttat catatatata gtccattatg ttcacattta gaatgatgtt    360
aacaattgtt ttgacatttt taaaatgaaa aactcatata tctagttcat gaaattgtta    420
ataaactaga aaatatatgg acataaaaat gacattagcc aagatatgat aatgaggcaa    480
tggtggcagg gtacacaagg cataaaagcc attatttccc acccaaaatg ttatgtcaca    540
tttgtgcctt actcagctat aatttatgta aaaatctgat ttgtgaatta agataactt     600 ttaaaagatt gtacaaaggt atatctacat ttttgaattg aactagagat gggaattatc    660
atgtcgtatt aaccactaca ttaaaaacac ttaagtatat ctagggcata aaaataaaaa    720
tcgatgtaat ggcacttaag atatgtatta a                                   751
```

EXPRESSION SYSTEM WITH SAR ELEMENT FROM IFNα2

RELATED APPLICATIONS

This application is a national stage filing under 35 U.S.C. §371 of International Patent Application PCT/CA2012/000254 filed Mar. 20, 2012, which claims the benefit of U.S. Provisional Application Ser. No. 61/474,879 filed Apr. 13, 2011, the disclosure of each of which is incorporated by reference herein in its entirety.

FIELD OF THE INVENTION

The present invention relates to polynucleotides for enhancing protein expression and to expression systems comprising the polynucleotides.

BACKGROUND OF THE INVENTION

High level and stable recombinant protein (r-protein) production in mammalian cells is important for cost-effective biotherapeutic manufacturing. S/MARs (Scaffold/Matrix Attachment Regions) are 70% AT-rich sequences, which are believed to play many important roles in chromatin function. In addition to their structural function, S/MARs play important roles in temporal and spatial organization of gene expression (Alvarez 2000; Liu 1997). The inclusion of an S/MAR sequence in an expression vector can thus help increase the level of expression and prevent silencing of the transgene (Phi-Van 1990; Jenke 2004; Zahn-Zabal 2001; Kim 2004). MAR elements have been shown to work either after integration into the host genome or as part of episomal vectors (Halweg 2005; Girod 2005).

Genomic elements such as UCOE (from Millipore) or MAR (from Selexis) are available and have proven to enhance expression level and stability when provided in cis or in trans in expression vectors used to generate stable cell lines. There are many S/MARs in the human genome that can be incorporated into expression vectors for enhancing productivity and stability of clonal cell lines (Girod 2007). However, not all of these sequences show beneficial effects (Sass 2005) and these sequences are very often very large (1.5 to 4 kb) and as such not practical to incorporate in expression vectors. There is a need to identify S/MAR sequences that are short (<1 kb) while still efficient, but the only way to achieve this is through a trial-and-error approach.

SUMMARY OF THE INVENTION

It has now been found that a short human genomic nucleotide sequence from the SAR3 region of the human interferon α2 gene permits enhanced expression stability in the absence of drug selection and permits generation of stable clones or stable pools of cells for producing recombinant proteins. Although stable clones may be generated, the ability to generate stable pools reduces the burden of generating stable clones.

Thus, in one aspect of the present invention there is provided an isolated polynucleotide comprising no more than 755 nucleotides and comprising at least 500 contiguous nucleotides from the nucleotide sequence as set forth in SEQ ID NO: 1.

In another aspect of the present invention there is provided an expression system for producing recombinant protein in a host cell comprising: a gene for encoding a protein of interest; nucleotide sequences for operation of the expression system; and, an expression enhancer incorporated in cis in the expression system for enhancing expression of the gene, the expression enhancer comprising a nucleotide sequence from human interferon alpha2 upstream scaffold associated region 3 (SAR3) comprising no more than 755 nucleotides and comprising at least 500 contiguous nucleotides from the nucleotide sequence as set forth in SEQ ID NO: 1.

In another aspect of the present invention, there is provided a host cell comprising the expression system of the present invention.

In another aspect of the present invention, there is provided a method of producing recombinant protein comprising: transfecting a host cell with an expression system of the present invention; growing the host cells under conditions suitable for expression of the gene to produce the protein of interest; and, recovering the protein of interest.

In another aspect of the present invention, there is provided a use of the polynucleotide of the present invention as an expression enhancer in cis in an expression system for producing recombinant protein.

The isolated polynucleotide comprises no more than 755 nucleotides and comprises at least 500 contiguous nucleotides from the nucleotide sequence as set forth in SEQ ID NO: 1. Preferably, the isolated polynucleotide comprises at least 550, 600, 650, 700 or 750 contiguous nucleotides from the nucleotide sequence as set forth in SEQ ID NO: 1. The isolated polynucleotide may be incorporated in cis in the expression system for enhancing r-protein expression in host cells transfected with the expression system. Advantageously, the expression enhancement is realized even in the absence of drug selection.

The expression system comprises a gene for encoding a protein of interest. Some particular proteins of interest include, for example, monoclonal antibodies (e.g. trastuzumab), erythropoietins, interferons, vascular endothelial growth factors, stem cell growth factors, growth hormones, insulin-like growth factor binding proteins, regulatory proteins (e.g. cumate operator, tetracycline repressor, steroid hormone receptors, transmembrane receptors), etc. The amino acid sequences of proteins of interest and the nucleotide sequences of the genes that encode such proteins are generally known in the art.

The expression system may comprise any suitable vector, for example plasmid vectors, episomal vectors (e.g. oriP/EBV vectors), viral vectors (e.g. Bacman) and cosmid vectors. The type of vector utilized in the expression system will depend on the intended host cell, among other factors, which can be readily determined by one skilled in the art. The vector comprises various nucleotide sequences for operation of the expression system. Such nucleotide sequences include, for example, promoters, origins of replication (e.g. bacterial origin of replication (pMBlori), Epstein-Barr Virus origin of replication (oriP)), leaders (e.g. adenovirus tripartite leader (TPL)), splice donors (SD), introns possibly including other enhancers (e.g. adenovirus major late promoter enhancer (Enh MLP)), splice acceptors (SA), selectable markers (e.g. antibiotic resistance genes), cloning sites (preferably multiple cloning sites) with restriction enzyme consensus sites (preferably multiple restriction enzyme consensus sites, e.g. EcoRV, Cla1, Sfol), and polyadenylation signals (e.g. rabbit beta-globin polyadenylation signal (pA)), among others. The expression system preferably comprises a plasmid vector.

Promoters are useful for controlling expression of various protein-encoding polynucleotides in the expression system. Strong or weak promoters may be used. Some promoters include, for example, cytomegalovirus (CMV) promoters, simian virus 40 promoter (SV40p), Elongation Factor 1 alpha-HTLV (EF1α-HTLV) hybrid promoter and Rous sarcoma virus (RSV) promoter. Selectable markers allow the selection of positively transfected cells. Common selectable markers include, for example, antibiotic resistance genes such as puromycin and hygromycin B for eukaryotic cells, and ampicilin and kanamycin for prokaryotic cells.

The expression system of the present invention may be transfected into a host cell by any suitable method. Such methods are generally known in the art (Kim 2010). The host cell is preferably a eukaryotic cell, more preferably a mammalian cell, for example, a Human Embryonic Kidney 293 (HEK293) cell, a Chinese Hamster Ovary (CHO) cell, a Baby Hamster Kidney (BHK21) cell, a PerC6 cell or a COS7 cell. Human Embryonic Kidney 293 (HEK293) and Chinese Hamster Ovary (CHO) cells are particularly preferred.

Transfected host cells are grown under conditions suitable to permit expression of the polynucleotide for encoding the protein of interest. Such conditions are generally well known for known host cells, for example mammalian cells such as HEK and CHO cells. Growth of cells is typically done in a culture medium and recovering the protein of interest from the cultured cells may also be conveniently done by known methods (Hauser 1997).

Advantageously, the isolated polynucleotide of the present invention can enhance stable expression in host cells when incorporated in cis in an expression system, permits enhanced expression stability in the absence of drug selection, can be combined with an episomal expression system (e.g. an oriP/EBNA1 system) for enhancing expression stability in the absence of drug selection even though pools generated with an episomal expression system (e.g. an oriP/EBNA1 system) are not stable without selection, and permits generation of stable pools for producing r-proteins without the burden of generating stable clones.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

EXAMPLE 1

Synthesis of SAR-BRI

Figure 2:
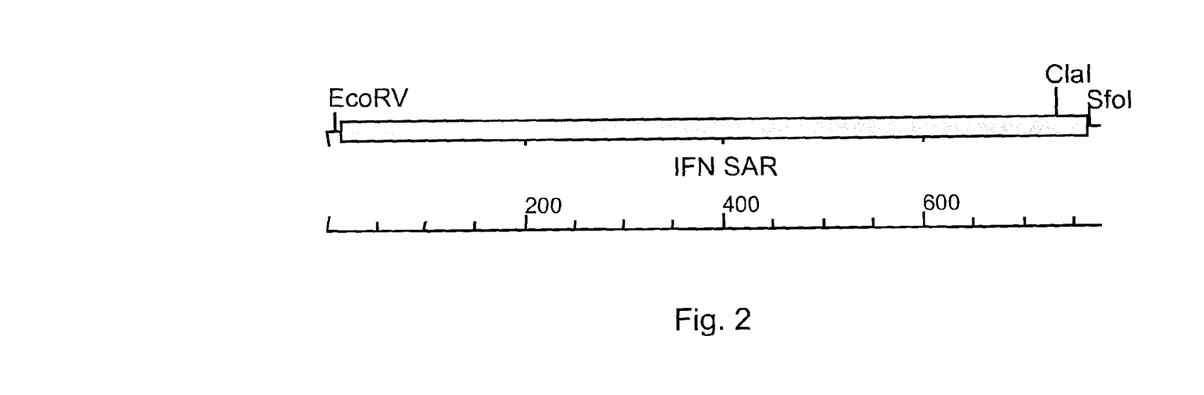
FIG. 2 depicts a restriction map of a SAR of the present invention showing the location of EcoRV and SfoI restriction sites.

An example of a SAR of the present invention (SAR-BRI) is set forth in SEQ ID NO: 1, which is a 751 nucleotide sequence corresponding to by numbers 1000-1750 of the human interferon α2 upstream scaffold associated region 3 (SAR3) sequence (gi|1791229|gb|U82705.1|HSU82705). SEQ ID NO: 1, which is 73.4% AT-rich (38.9% A, 34.5% T, 12.2% C, 14.4% G), was identified as a potential expression insulator and Geneart was contracted to synthesize it using generally known methods. The sequence possesses two base mutations that were generated to destroy endogeneous EcoRI and EcoRV restriction sites (C1639→G and G1695→T, respectively). The sequence was also flanked by EcoRV and SfoI restriction sites on the 5' and 3' ends, respectively, for cloning purposes, as shown in FIG. 2.

Figure 1A:
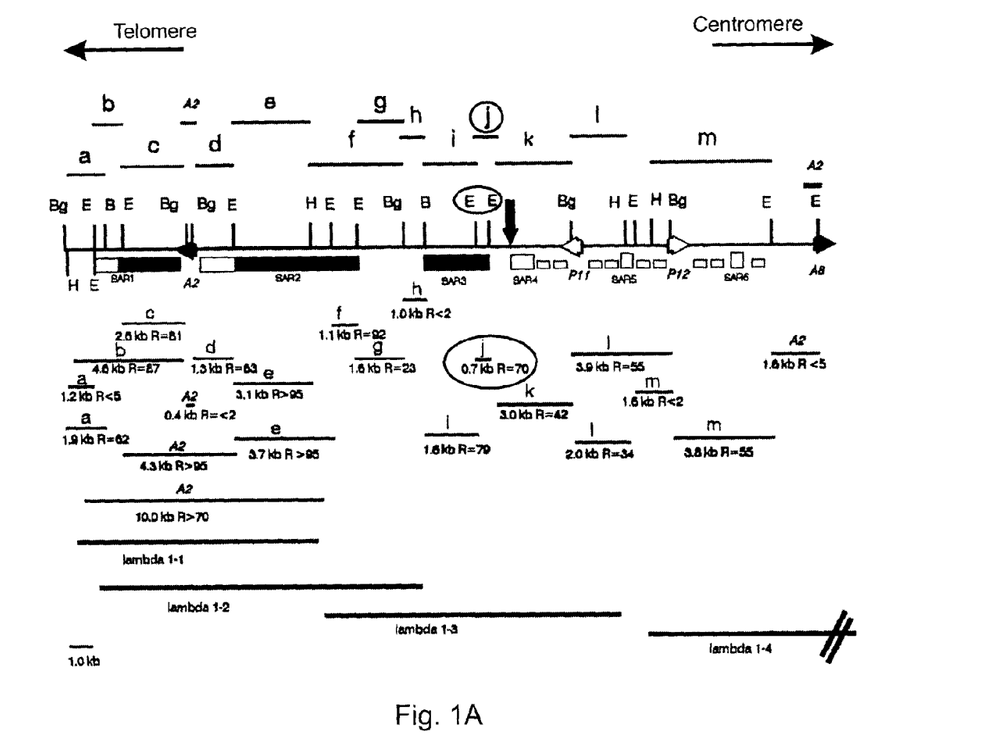
FIG. 1A depicts a restriction enzyme map taken from the prior art (FIG. 1a in Strissel 1998) of the human interferon α2 gene showing the location of various scaffold associated regions, including the upstream scaffold associated region 3 (SAR3). The two EcoRI sites are indicated by "E" and are circled. A 0.7 kb SAR identified by Strissel in the SAR3 region is indicated by "j, R=70" and is also circled.
Figure 1B:
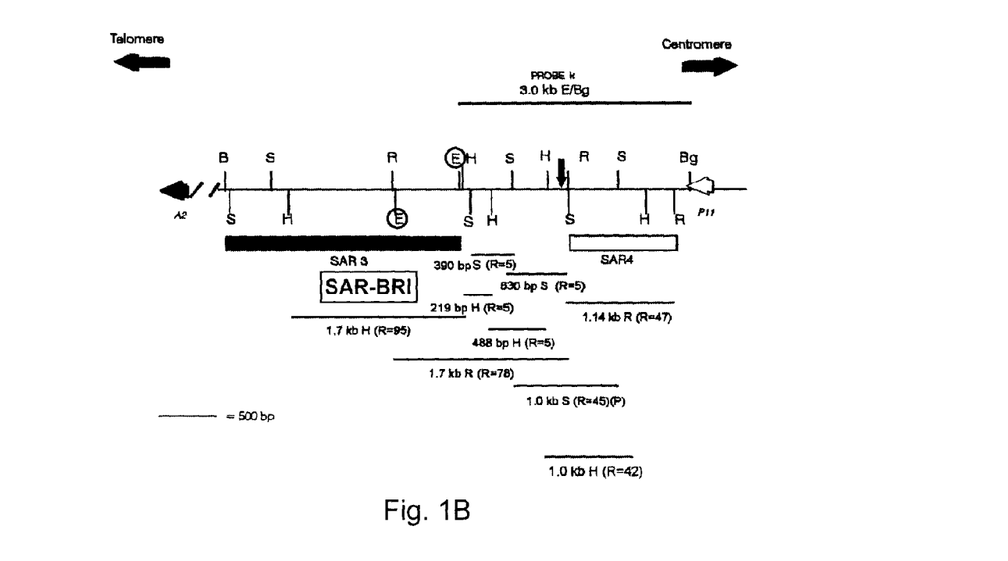
FIG. 1B depicts a restriction enzyme map taken from the prior art (FIG. 1c in Strissel 1998) showing the SAR3 region of human interferon α2 gene, and showing where the SAR of the present invention (SAR-BRI) is located on the map.
Figure 1C:
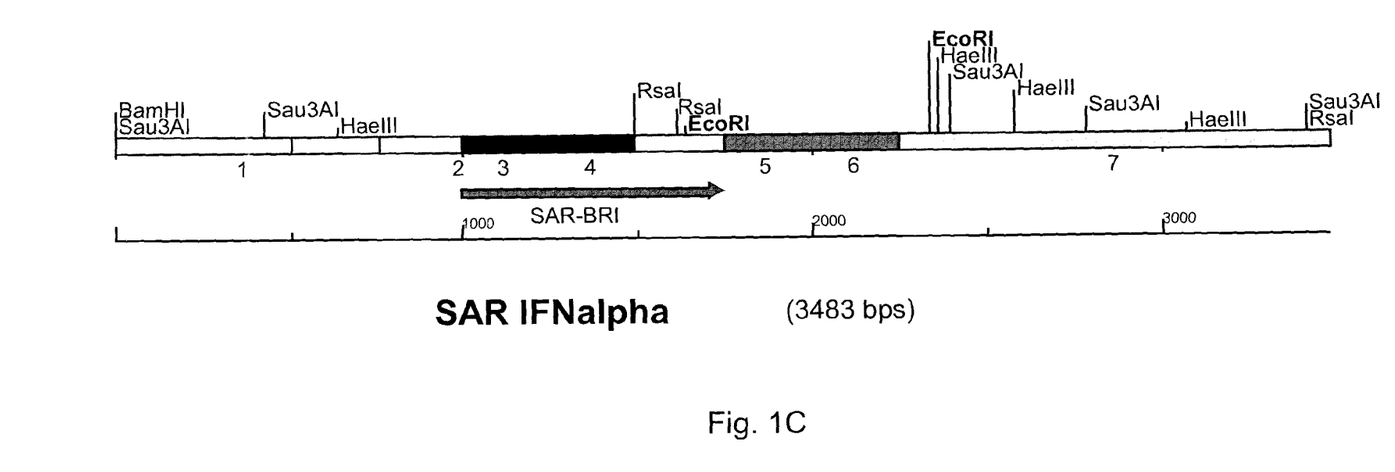
FIG. 1C depicts a map of a 3483 bp upstream region of SAR IFNα showing the location of the SAR-BRI in relation to restriction sites in the region.

Previously, a 0.7 kb "strong" SAR element from the SAR3 region of IFN-α2 was identified (Strissel 1998). As shown in FIG. 1A, this 0.7 kb SAR (j, R=70) is located between two EcoRI sites (circled E's). In contrast, the SAR of the present invention (SAR-BRI) is located upstream of the second EcoRI site and ends just after the first EcoRI site as shown in FIG. 1B. The location of SAR-BRI in SAR3 encompassing bps 1000-1750 of the 3483 bp SAR IFNα sequence is further depicted in FIG. 1C. It is clear from FIG. 1 that the SAR of the present invention (SAR-BRI) does not correspond to the 0.7 kb SAR identified by Strissel (j, R=70).

Further, the strength of the SARs disclosed in Strissel 1998 is based on repartion of the DNA fragment between the pellet (nuclei) fraction and the supernatant, as indicated in the Strissel reference:

"The relative strength (R) of each individual DNA fragment to partition in the pellet fraction was estimated as the band intensity in the pellet divided by the sum of intensities of pellet plus supernatant (R=IP/IP+IS). R values were determined on previously published SAR and non-SAR DNA fragments, all of which were hybridized to the same Southern blots simultaneously to set standards for binding affinity (see Table 1 in Strissel et al. 1996). R values set for strong SAR DNA fragments represent 70% (R>70) enrichment into the pellet fraction, for example, the B1 5* SAR (detected with the . . . "

Therefore, Strissel does not provide functional in vivo activity of the 0.7 kb SAR per se, meaning that the in vivo strength of the SAR identified in Strissel 1998 is unknown.

EXAMPLE 2

Erythropoietin (EPO) Expression Plasmids

Figures 3A, 3B:
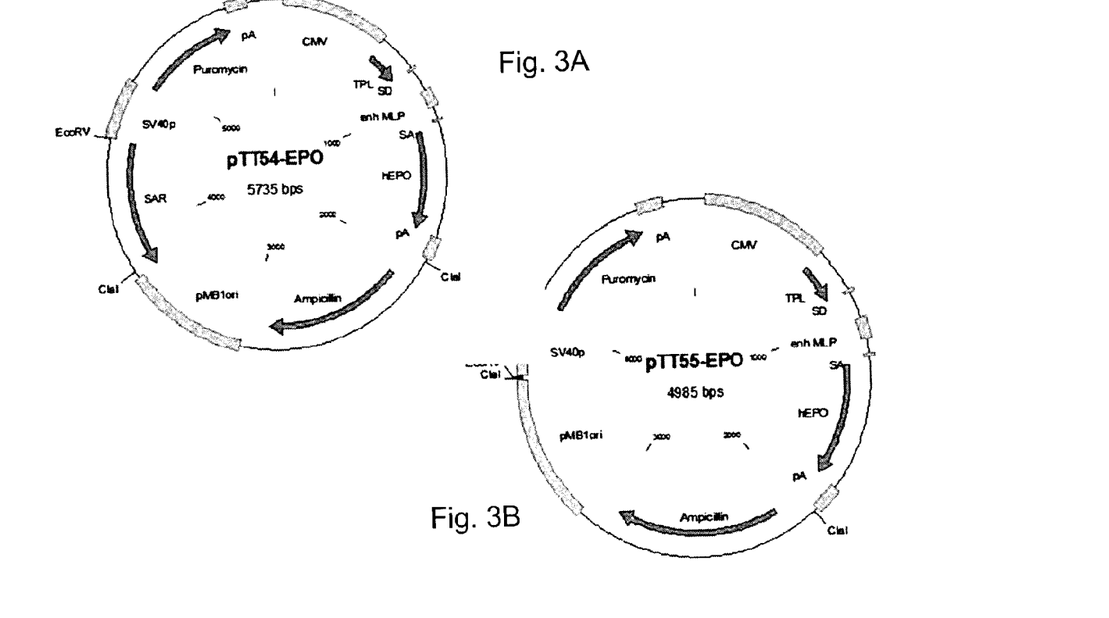
FIG. 3A depicts a vector map of pTT54-EPO plasmid containing SAR-BRI.
FIG. 3B depicts a vector map of pTT55-EPO plasmid not containing SAR-BRI.

The SAR-BRI sequence synthesized in Example 1 was inserted in a pTT55-EPO vector (FIG. 3B) at the EcoRV restriction site lying between the puromycin resistance cassette and the prokaryotic origin of replication (pMB1) to yield pTT54-EPO plasmid (FIG. 3B). The pTT55-EPO plasmid encodes a codon-optimized human erythropoietin cDNA (Geneart) under the control of the CMV5 promoter (Durocher 2002; Massie 1998).

The pTT55-EPO and pTT54-EPO plasmids were transfected into Chinese Hamster Ovary (CHO) cells and the cells were cultured under puromycin selection to form stable CHO-DG44 EPO pools. To generate the CHO-DG44 pools expressing EPO, cells grown in CHO CD-DG44 medium (Invitrogen) were transfected with PEImax (Polysciences) using 1 µg/ml of supercoiled plasmid DNA at a DNA:PEI ratio of 1:5 (w:w). Puromycin was then added 24 hours post-transfection (hpt) at a concentration of 10 µg/ml. The culture medium was regularly replaced with fresh medium containing puromycin for over 60 days.

Figure 3C:
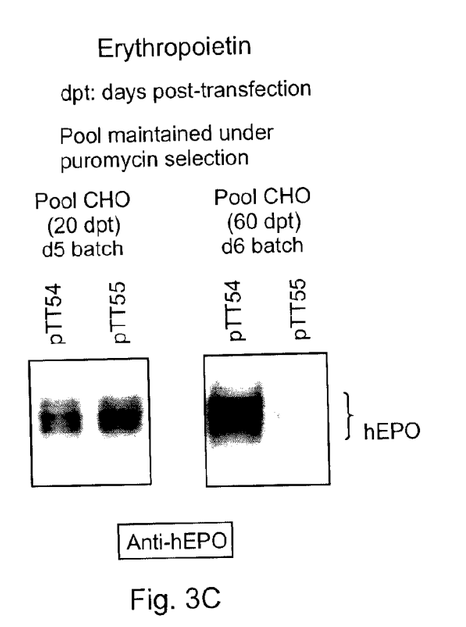
FIG. 3C depicts western blots of CHO-DG44 pools transfected with pTT54-EPO and pTT55-EPO and expressing EPO, 20 days post-transfection (left) and 60 days post-transfection (right).

After 20 and 60 days post-transfection, EPO expression between pools generated with pTT54-EPO and pTT55-EPO vectors was compared (FIG. 3C). To do so, cells where transferred in a new flask at a density of $0.2 \times 10^6$ cells/ml in fresh medium and the culture was maintained for 5-6 days. A sample of the culture medium was then analyzed by western blot using an anti-EPO antibody (FIG. 3C). Due to its extensive and heterogeneous glycosylation, EPO migrated as multiple bands (smear) on SDS-PAGE.

It is evident from FIG. 3C that CHO cells transfected with pTT54-EPO containing the SAR-BRI of the present invention are capable of expressing r-protein at high levels over a longer period of time. While both the pTT54-EPO plasmid and pTT55-EPO plasmid provide good expression 20 days post-transfection (left blot), only pTT54-EPO having the SAR-BRI provided significant r-protein expression 60 days post-transfection (right blot). This demonstrates that use of a SAR of the present invention permits generation of stable pools for producing r-proteins without the need for generating stable clones.

Figure 3D:
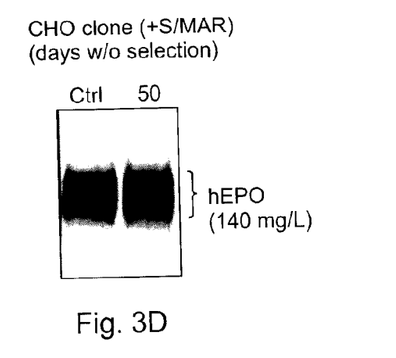
FIG. 3D depicts a western blot of a pTT54-EPO clone (+S/MAR element) maintained for 50 days without selection (right lane) compared to a control (Ctrl) batch of freshly thawed pTT54-EPO clone (+S/MAR element) (left lane).

Further, an EPO clone (+S/MAR element) maintained for 50 days without selection was compared in parallel to a freshly thawed batch of EPO clone (+S/MAR element) as a control (Ctrl). The western blot (FIG. 3D) shows similar productivity (140 mg/L) for both indicating that the clone is very stable.

Figure 3E:
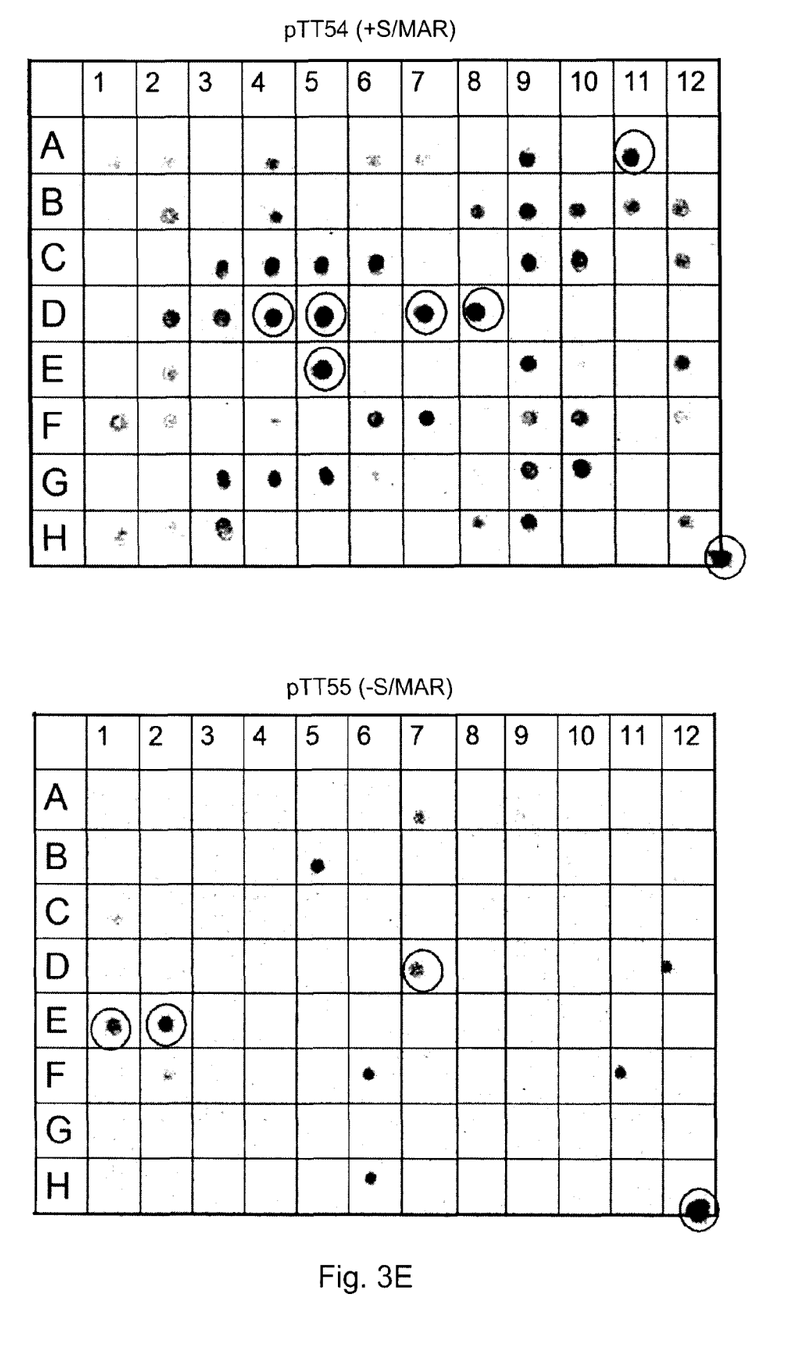
FIG. 3E depicts dotblots of the supernatant from cell cultures of cells transfected with pTT54-EPO (upper) and pTT55-EPO (lower), in which the presence of EPO in the supernatant is detected using an anti-EPO antibody.

Furthermore, cells from the pools obtained with pTT54-EPO and pTT55-EPO vectors were plated at low cell density in semi-solid medium (Caron 2009) in the absence of selection. Once the colonies reached 4-10 cells, these were randomly picked and transferred into 96-well plates. After one week in culture, an aliquot of the supernatant from each well was spotted on a nitrocellulose membrane and the presence of EPO detected using an anti-EPO antibody. It is clear from FIG. 3E that the number of positive clones is higher with cells transfected with pTT54-EPO containing the SAR-BRI (upper dotblot). Also most of the clones obtained with the SAR-BRI express more EPO than without the SAR. EPO standards comprising the same quantity of EPO deposited on all membranes are shown in grid location H12 on each dotblot. Longer exposure was needed in the pTT55 not containing the SAR-BRI.

These results demonstrate that use of a SAR of the present invention permits generation of stable clones for producing r-protein at high levels.

EXAMPLE 3

HERCEPTIN expression plasmids

Figure 4A:
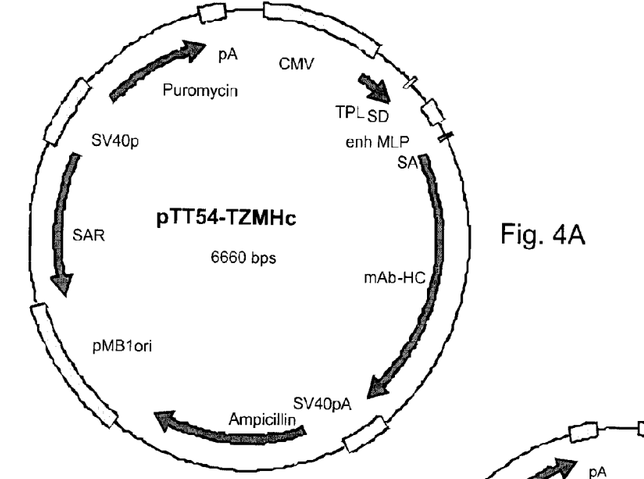
FIG. 4A depicts a vector map of pTT54-TZMHc plasmid containing SAR-BRI.
Figures 4B, 4C:
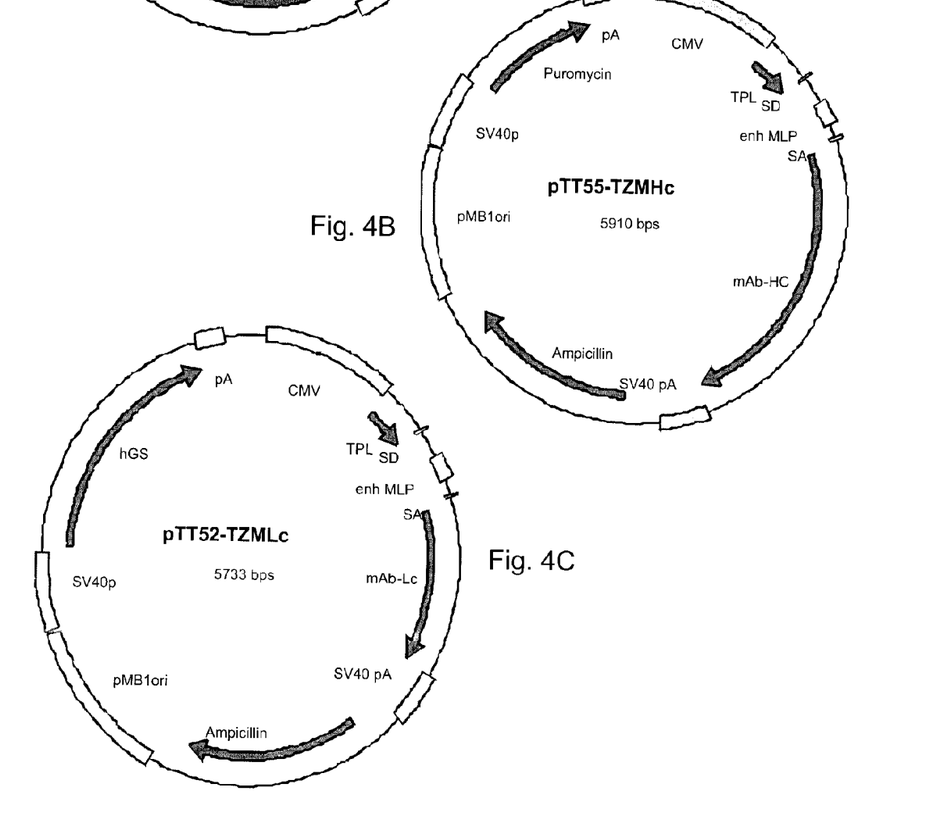
FIG. 4B depicts vector map of pTT55-TZMHc plasmid not containing SAR-BRI.
FIG. 4C depicts vector map of pTT52-TZMLc plasmid not containing SAR-BRI.

HERCEPTIN is a trade name for the monoclonal antibody trastuzumab. Codon-optimized HERCEPTIN heavy chain cDNA (Geneart) was cloned into pTT54 or pTT55 vectors to yield pTT54-TZMHc plasmid (FIG. 4A) and pTT55-TZMHc plasmid (FIG. 4B). The HERCEPTIN light chain was cloned into pTT52 vector to yield pTT52-TZMLc plasmid (FIG. 4C). The pTT52 vector is the same as the pTT55 vector except that the puromycin resistance gene was replaced by a glutamine synthase gene (hGS). The pTT54-TZMHc plasmid contains the SAR-BRI sequence while pTT55-TZMHc and pTT52-TZMLc do not.

Figure 4D:
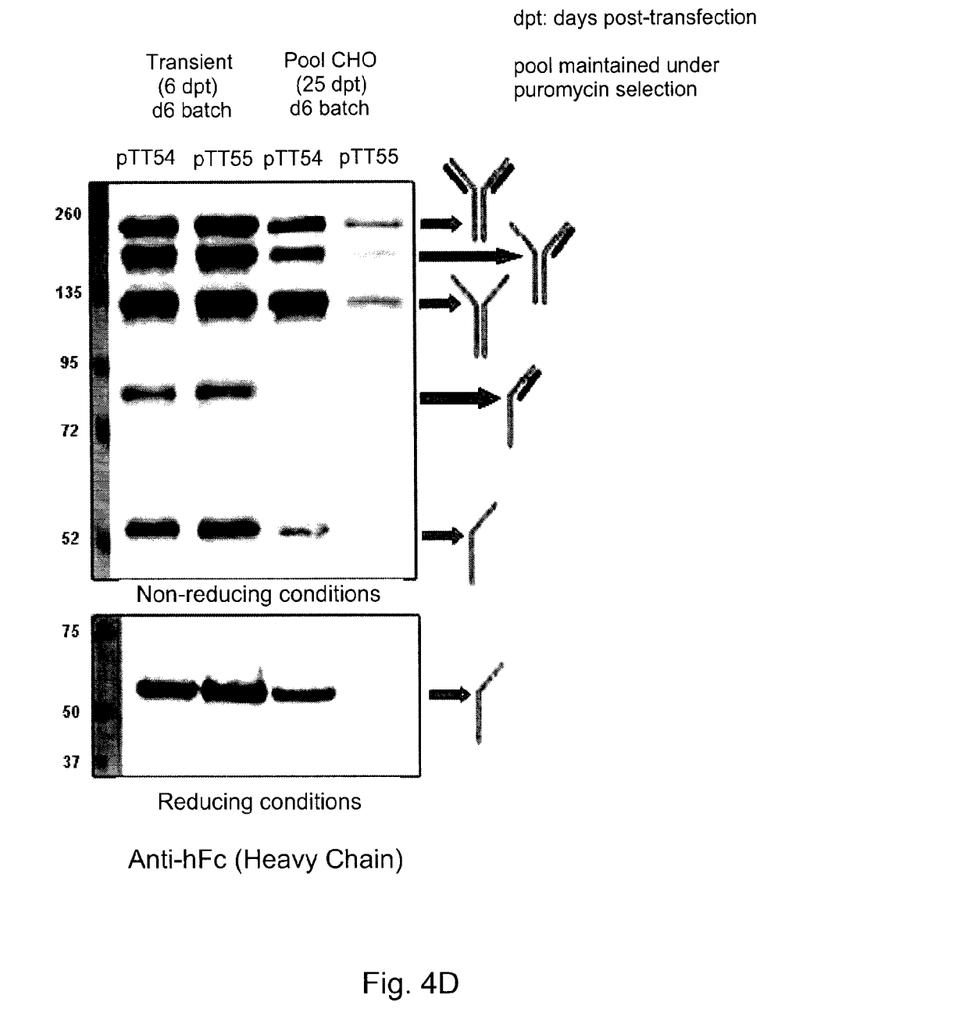
FIG. 4D depicts western blots comparing of CHO-DG44 pools transfected with pTT54-TZMHc+pTT52-TZMLc and pTT55-TZMHc+pTT52-TZMLc expressing Herceptin™, 6 days post-transfection (left) and 25 days post-transfection (right).

To generate stable CMO-DG44 pools expressing HERCEPTIN, cells were transfected as described for EPO in Example 2 except that two vectors were co-transfected at a 1:1 (w:w) ratio (pTT54-TZMHc+pTT52-TZMLc or pTT55-TZMHc+pTT52-TZMLc). Selection was done as for EPO. Expression of HERCEPTIN by the resulting pools was compared 6 days or 25 days post-transfection by western blot under reducing or non-reducing condition using an anti-hFc antibody (FIG. 4D). The presence of partially disassembled antibody species on SDS-PAGE may be due to disulphide bond reduction during the culture and has been already described (Trexler-Schmidt 2010).

It is evident from FIG. 4D that CHO cells transfected with pTT54-TZMHc containing the SAR-BRI of the present invention are capable of expressing r-protein at high levels over a longer period of time. While both the pTT54-TZMHc plasmid and pTT55-TZMHc plasmid provide good expression 6 days post-transfection (left blot), only pTT54-TZMHc having the SAR-BRI provided significant r-protein expression 25 days post-transfection (right blot). This further demonstrates that the use of a SAR of the present invention permits generation of stable pools for producing r-proteins without the need for generating stable clones. Since EPO pools generated with the SAR-BRI sequence (Example 2, FIG. 3E) provide higher frequency of high-expressing EPO clones, it is expected that higher frequency of high-expressing Herceptin™ clones would also be observed in the presence of the SAR-BRI element.

EXAMPLE 4

EG2 cHCAb Expression Plasmids

Figure 5A:
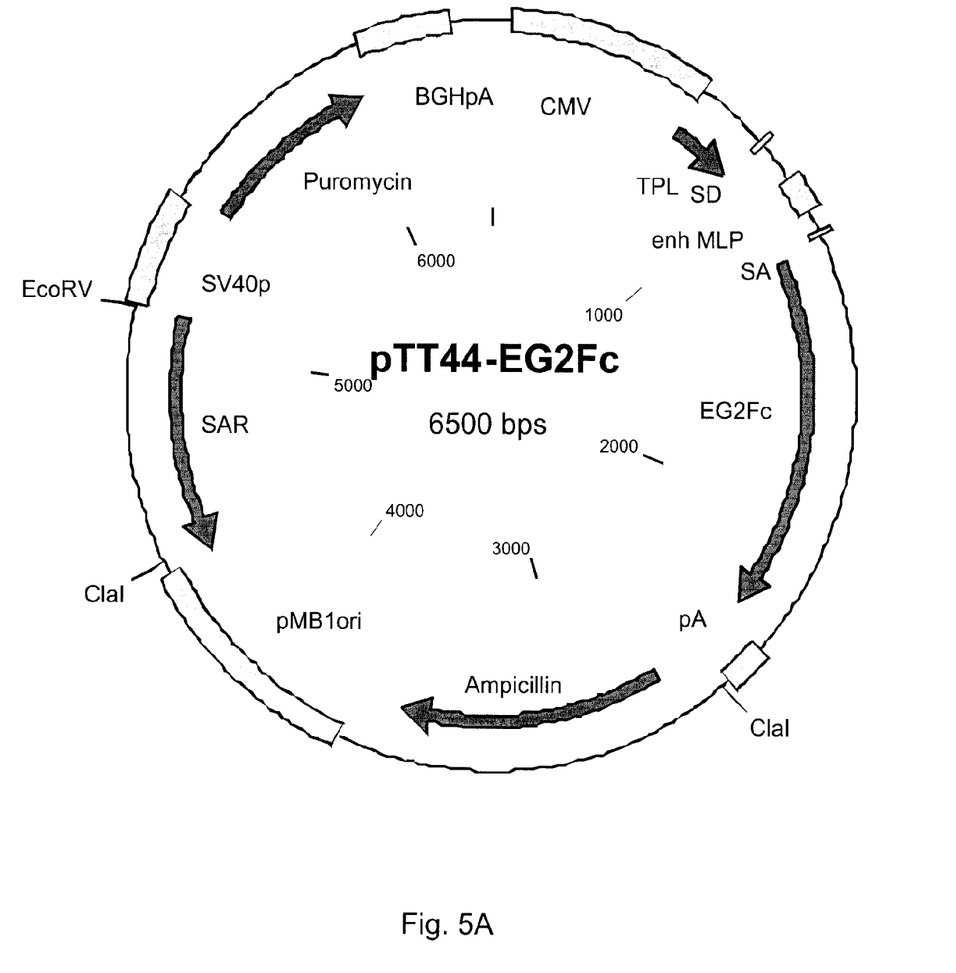
FIG. 5A depicts a vector map of pTT44-EG2Fc plasmid containing SAR-BRI.

The chimeric heavy chain antibody EG2 (Zhang 2009) was cloned into pTT44 vector to yield pT44-EG2Fc plasmid (FIG. 5A). The pT44 vector is identical to the pTT54 vector except for the puromycin polyadenylation signal which is from the bovine growth hormone instead of the rabbit beta-globin.

To generate CHO-DG44 clones expressing EG2Fc, cells were transfected as described for EPO in Example 2 except that the plasmid was linearized by digestion with PvuI enzyme. Following transfection, cells were selected in the presence of 10 µglml of puromycin for eight days. Then, puromycin resistant cells were plated at a density of 250 cells/ml in a semi-solid medium without puromycin selection as previously described (Caron 2009). The presence of EG2Fc was monitored by inclusion of fluorescent-labeled anti-IgG antibodies in the semi-solid medium and clones expressing high levels of the cHCAb were identified by fluorescence microscopy and transferred in 96 well-plates using a CELLCELECTOR clone picker (Caron 2009).

Figure 5B:
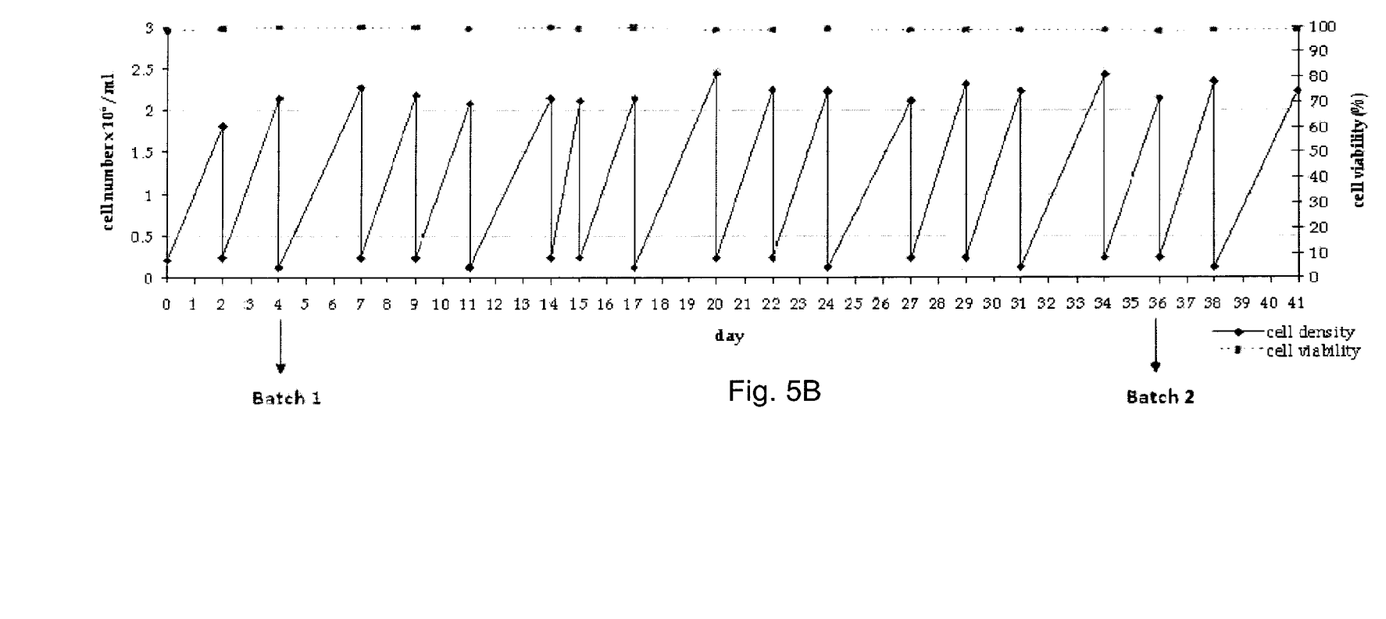
FIG. 5B depicts a maintenance schedule for CHO-DG44-EG2Fc (clone 1A7) cells over 41 days without selection.
Figure 5C:
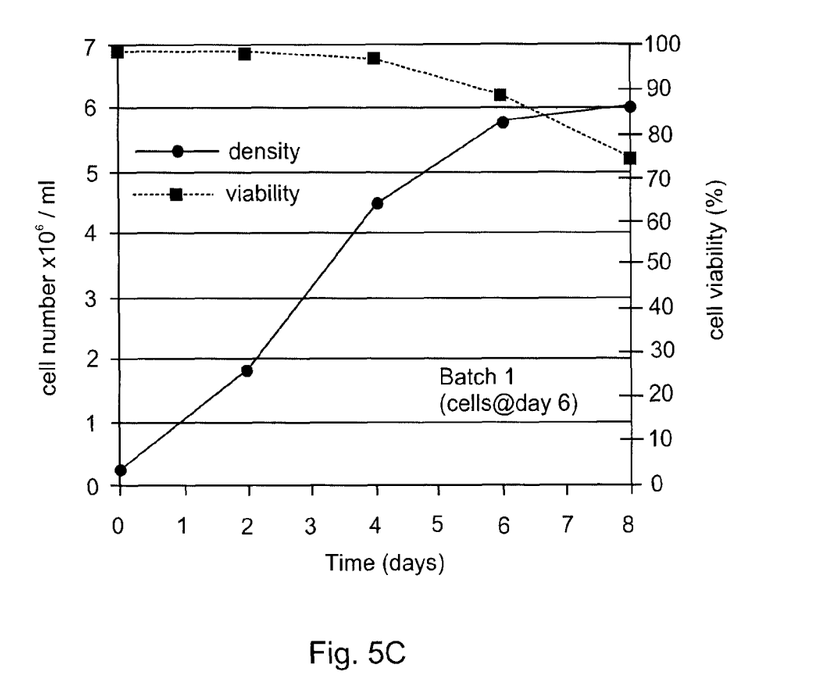
FIG. 5C depicts a graph showing cell density and viability of CHO cells maintained as in FIG. 5B and then transferred at day 4 (Batch 1) into a new culture flask and cultured for another 8 days.
Figure 5D:
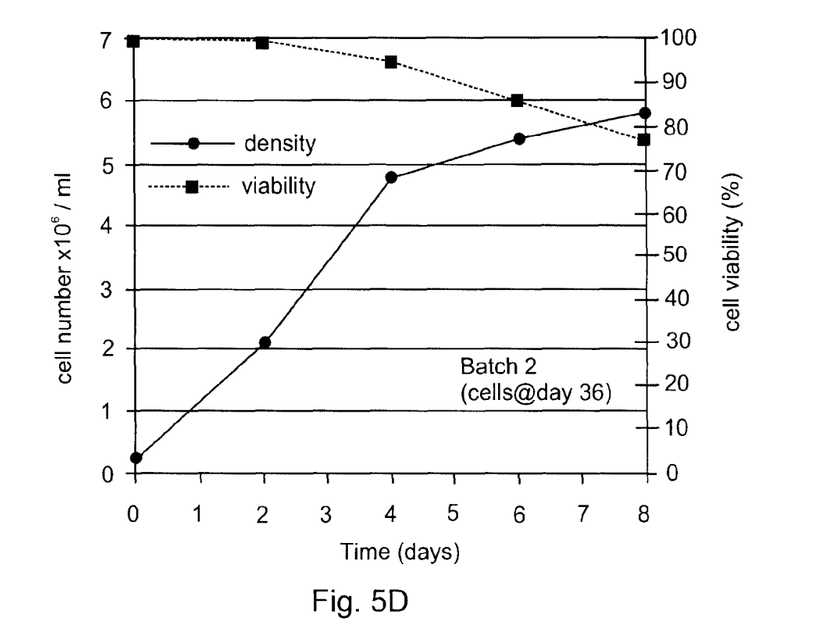
FIG. 5D depicts a graph showing cell density and viability of CHO cells maintained as in FIG. 5B and then transferred at day 36 (Batch 2) into a new culture flask and cultured for another 8 days.

As depicted in FIG. 5B, one clone (1A7) was selected for high productivity, further expanded and a Master Cell Bank (MCB) was made. Following thawing of one vial from the MCB, productivity was assessed after extensive culture of this clone in suspension without puromycin selection. To do so, cells were transferred at day 4 (Batch 1) and day 36 (Batch 2) post-thawing to a new flask and cultured for 8 days. FIGS. 5C and 5D demonstrate that the new cultures for both Batch 1 (FIG. 5C) and Batch 2 (FIG. 5D) were still very similar in terms of viability and total cell density.

Figure 5E:
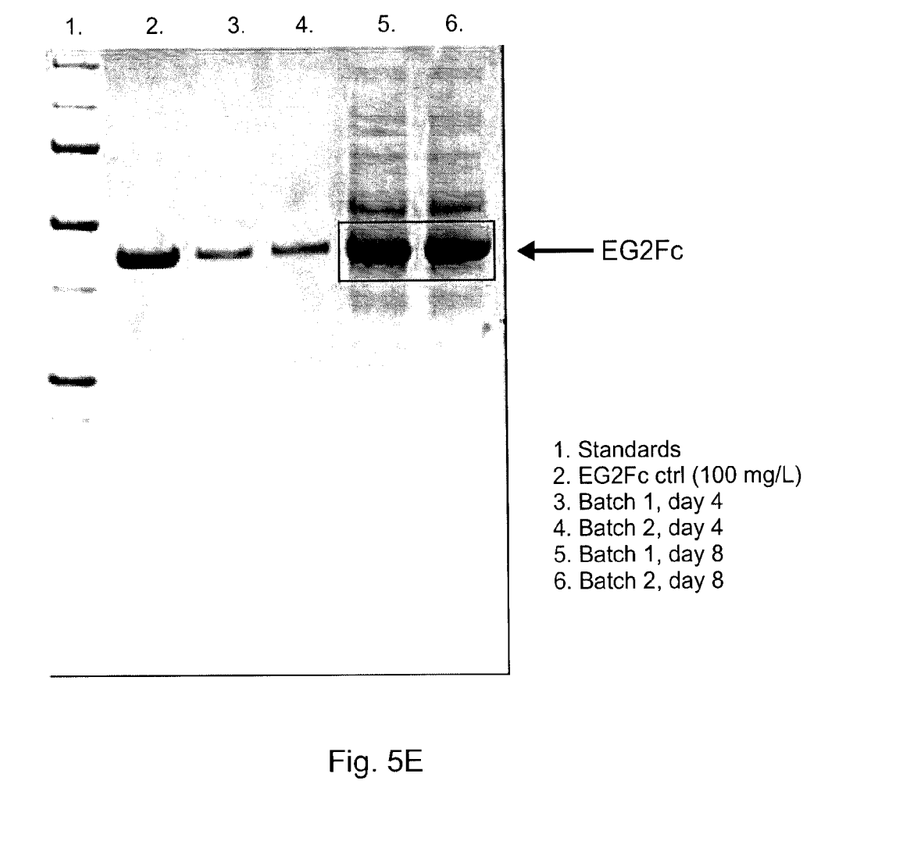
FIG. 5E depicts SDS-PAGE with Coomassie staining for determining EG2Fc titers in Batch 1 and Batch 2 cultures after 4 days and 8 days.

EG2Fc titers in Batch 1 and Batch 2 cultures after 4 days and 8 days were compared by SDS-PAGE and Coomassie staining (FIG. 5E). A purified EG2Fc control (Lane 2 in FIG. 5E) at 100 mg/L was loaded in parallel for comparison purpose. It is evident from FIG. 5E that after 4 days of culturing the cells without selection pressure (Lanes 3 and 4), r-protein expression was evident and that after 8 days (Lanes 5 and 6), r-protein expression levels were very high. As productivity was very similar whether cells were taken from an early (day 4) or late (day 36) passage in the absence of selection, this demonstrates that the use of a SAR of the present invention leads to robust expression stability in clones even in the absence of drug selection pressure.

EXAMPLE 5

SAR-BRI in an Epstein-Barr Virus (EBV) Episome

It is well known that EBV's episomes are lost at a rate of 1-4% per generation in the absence of selection pressure (Lindner 2007). To enhance retention of EBV episomes, attempts to combine a S/MAR element to an oriP plasmid have hitherto failed (Giannakopoulos 2009).

Pools of HEK293-EBNA1 cells transfected with the oriP-containing pTT22-GFP vector lose GFP expression when selection pressure is removed after 72 days in culture. However, in preliminary unpublished studies, the inclusion of one or two S/MAR sequences from human beta-globin and/or beta-interferon in the pTT22-GFP vector enhances episome stability upon removal of selection pressure as significantly higher percentage of GFP-positive cells can be observed after 125 days (53 days without selection). Likewise, it is expected that the inclusion of SAR-BRI in an episomal vector will also enhance episome stability upon removal of selection pressure.

Free listing of sequences:

```
                                                 SEQ ID NO: 1
751 nucleotides corresponding to bp 1000 to 1750
of gb#0U82705.1
AATCAGAGAAACAAAAATGTTAGAAAATTCTTGCAGGTGATTTTCAATAT
TGTTTTATTTTGTGCAAAAAATAATTAACCTTTTAGAAGGTCCCAGAGTA
TTAGAAGCCCAAACTCTGGAATATTCTCAATTTTAGTTGAGCTTTTCAGT
TATTATAATATTGTATAGCTACTCATATAATTAGTAATACAAAAGATTCT
GAGTCTTATTTGTAAATAAAGTTCAAAATAAGTCATATGTTATATGTTAT
AGGTAATCATGTTAGATATAAACCACTATTGAAAAAGATATAAAAACAAA
ATAACTTTATTTTTGTTATCATATATATAGTCCATTATGTTCACATTTA
GAATGATGTTAACAATTGTTTTGACATTTTTAAAATGAAAAACTCATATA
TCTAGTTCATGAAATTGTTAATAAACTAGAAAATATATGGACATAAAAAT
GACATTAGCCAAGATATGATAATGAGGCAATGGTGGCAGGGTACACAAGG
CATAAAAGCCATTATTTCCCACCCAAAATGTTATGTCACATTTGTGCCTT
ACTCAGCTATAATTTATGTAAAAATCTGATTTGTGAATTAAGATAACTTT
TTAAAAGATTGTACAAAGGTATATCTACATTTTTGAATTGAACTAGAGAT
GGGAATTATCATGICGTATTAACCACTACATTAAAAACACTTAAGTATAT
CTAGGGCATAAAAATAAAAATCGATGTAATGGCACTTAAGATATGTATTA
A
```

References: The contents of the entirety of each of which are incorporated by this reference.

Alvarez J D, et al. (2000) The MAR-binding protein SATB1 orchestrates temporal and spatial expression of multiple genes during T-cell development. *Genes & Development.* 14(5), 521-35.

Bode J, Fetzer C P, Nehlsen K, Scinteie M, Hinrichsen B-H, Baiker A, Piechazcek C, Benham C, Lipps H J. (2001) The Hitchhiking principle: Optimizing episomal vectors for the use in gene therapy and biotechnology. *Gene Ther Mol Biol.* 6, 33-46.

Brosius J. (2008) The Effect of Putative Chromatin-Opening Element on the Methotrexate Amplification of CHO Cells. A Major Qualifying Project Report Submitted to the Worcester Polytechnic Institute published Jan. 9, 2008.

Caron A W, Nicolas C, Gaillet B, Ba I, Pinard M, Garnier A, Massie B, Gilbert R. (2009) Fluorescent labeling in semi-solid medium for selection of mammalian cells secreting high-levels of recombinant proteins. *BMC Biotechnol.* 9, 42.

Chatellard P, Imhof M. (2005) Minimal DNA Sequence Acting as a Chromatin Insulator and its Use in Protein Expression. International Patent Publication WO 2005-040384 published May 6, 2005.

Dang Q, Auten J, Plavec I. (2000) Human Beta Interferon Scaffold Attachment Region Inhibits De Novo Methylation and Confers Long-Term, Copy Number-Dependent Expression to a Retroviral Vector. *Journal of Virology.* 74(6), 2671-2678.

Daniell H. (2006) Expression of Human Interferon in Transgenic Chloroplasts. United States Patent Publication US 2006-0123515 published Jun. 8, 2006.

Durocher Y, Perret S, Kamen A. (2002) High-level and high-throughput recombinant protein production by transient transfection of suspension-growing human 293-EBNA1 cells. *Nucleic Acids Res.* 30(2), E9.

Durocher Y, Perret S, Pham P L, Kamen A. (2005) Enhanced Production of Recombinant Proteins by Transient Transfection of Suspension-Growing Mammalian Cells. United States Patent Publication US 2005/0170450 published Aug. 4, 2005.

Durocher Y. (2006) Expression Vectors for Enhanced Transient Gene Expression and Mammalian Cells Expressing Them. International Patent Publication WO 2006/096989 published Sep. 21, 2006.

Durocher Y. (2008) Expression Vectors Containing a Truncated Epstein Barr Nuclear Antigen 1 Lacking the Gly-Gly-Ala Domain for Enhanced Transient Gene Expression. United States Patent Publication 2008/0070232 published Mar. 20, 2008.

Enenkel B, Sautter K. (2008) Regulatory Nucleic Acid Elements. United States Patent Publication US 2008-0124760 published May 29, 2008.

Frey M. (2008) Polynucleotides for Enhancing Expression of a Polynucleotide of Interest. International Patent Publication WO 2008-116931 published Oct. 2, 2008.

GenBank Accession No. U82705.1. (1997) Human interferon alpha2 upstream scaffold associated region 3 (SAR3) and non-SAR region DNA Features.

Giannakopoulos A, Stavrou E F, Zarkadis I, Zoumbos N, Thrasher A J, Athanassiadou A. (2009) The Functional Role of S/MARs in Episomal Vectors as Defined by the Stress-Induced Destabilization Profile of the Vector Sequences. *J. Mol. Biol.* 387, 1239-1249.

Girod P A, Zahn-Zabal M, Mermod N. (2005) Use of the chicken lysozyme 5' matrix attachment region to generate high producer CHO cell lines. *Biotechnology and Bioengineering.* 91(1), 1-11.

Girod P A, et al. (2007) Genome-wide prediction of matrix attachment regions that increase gene expression in mammalian cells. *Nature Methods.* 4(9), 747-53.

Halweg C, Thompson W F, Spiker S. (2005) The rb7 matrix attachment region increases the likelihood and magnitude of transgene expression in tobacco cells: a flow cytometric study. *The Plant Cell.* 17(2), 418-29.

Hauser H, Wagner R. (1997) Mammalian cell biotechnology in protein production. Editors, Hansjörg Hauser and Roland Wagner. (Berlin, New York; Walter de Gruyter).

Jenke A C, et al. (2004) Expression of a transgene encoded on a non-viral episomal vector is not subject to epigenetic silencing by cytosine methylation. *Molecular Biology Reports.* 31(2), 85-90.

Jones T, Baker M, Hanlon M, Carr F J. (2007) Fusion Proteins of Interferon alpha Muteins with Improved Properties. United States Patent Publication US 2007-0148739 published Jun. 28, 2007.

Kim J M, et al. (2004) Improved recombinant gene expression in CHO cells using matrix attachment regions. *Journal of Biotechnology.* 107(2), 95-105.

Kim T K, Eberwine J H. (2010) Mammalian cell transfection: the present and the future. *Analytical and Bioanalytical Chemistry.* 397(8), 3173-3178.

Klehr D, Schlake T, Maass K, Bode J. (1992) Scaffold-Attached Regions (SAR Elements) Mediate Transcriptional Effects Due to Butyrate. *Biochemistry.* 31, 3222-3229.

Lindner S E, Sugden B. (2007) The plasmid replicon of Epstein-Barr virus: mechanistic insights into efficient, licensed, extrachromosomal replication in human cells. *Plasmid.* 58(1), 1-12.

Liu J, et al. (1997) The matrix attachment region-binding protein SATB1 participates in negative regulation of tissue-specific gene expression. *Molecular and Cellular Biology.* 17(9), 5275-87.

Lufino M M P, Edser P A H, Wade-Martins R. (2008) Advances in High-capacity Extrachromosomal Vector Technology: Episomal Maintenance, Vector Delivery, and Transgene Expression. *Molecular Therapy.* 16(9), 1525-1538.

Massie B, et al. (1998) New adenovirus vectors for protein production and gene transfer. *Cytotechnology.* 28(1-3), 53-64.

Mehtali M. (2008) Recombinant Protein Production in Avian EBx® Cells. European Patent Publication EP 1995309 published Nov. 26, 2008.

Mermod N, Girod P A, Calabrese D, Saugy D, Puttini S. (2005) High Efficiency Gene Transfer and Expression in Mammalian Cells by a Multiple Transfection Procedure of MAR Sequences. International Patent Publication WO 2005-040377 published May 6, 2005.

Mermod N, Girod P A, Calabrese D, Regamey A, Doninelli-Arope S. (2008) Matrix Attachment Regions (MARS) for Increasing Transcription and Uses Thereof. International Patent Publication WO 2008-023247 published Feb. 28, 2008.

Patten P A, Govindarajan S, Viwanathan S, Nissen T L. (2009a) Interferon-alpha Polypeptides and Conjugates. United States Patent Publication US 2009-0017502 published Jan. 15, 2009.

Patten P A, Govindarajan S, Viwanathan S, Nissen T L. (2009b) Interferon-alpha Polypeptides and Conjugates. United States Patent Publication US 2009-0042252 published Feb. 12, 2009.

Phi-Van L, et al. (1990) The chicken lysozyme 5' matrix attachment region increases transcription from a heterologous promoter in heterologous cells and dampens position effects on the expression of transfected genes. *Molecular and Cellular Biology.* 10(5), 2302-7.

Pomykala H M, Bohlander S K, Broeker P L, Olopade O I, Diaz M O. (1994) Breakpoint Junctions of Chromosome 9p Deletions in Two Human Glioma Cell Lines. *Molecular and Cellular Biology.* 14(11), 7604-7610.

Sass A V, Ruda V M, Akopov S B, Snezhkov E V, Nikolaev L G, Sverdlov E D. (2005) Regulatory Potential of S/MAR Elements in Transient Expression. *Russian Journal of Bioorganic Chemistry.* 31(1), 70-73.

Sperry A O, Blasquez V C, Garrard W T. (1989) Dysfunction of chromosomal loop attachment sites: Illegitimate recombination linked to matrix association regions and topoisomerase II. *Proc. Natl. Acad. Sci. USA.* 86, 5497-5501.

Strissel P L, Dann H A, Pomykala H M, Diaz M O, Rowley J D, Olopade O I. (1998) Scaffold-Associated Regions in the Human Type I Interferon Gene Cluster on the Short Arm of Chromosome 9. *Genomics.* 47, 217-229.

Treco D A, Heartlein M W, Selden R F. (1999) Genomic Sequences Upstream of the Coding Region of the IFN alpha2 Gene for Protein Production and Delivery. International Patent Publication WO 1999-057292 published Nov. 11, 1999.

Trexler-Schmidt M., et al. (2010) Identification and prevention of antibody disulfide bond reduction during cell culture manufacturing. *Biotechnology and Bioengineering.* 106(3), 452-61.

Winkelmann S, Klar M, Benham C, Prashanth A K, Goetze S, Gluch A, Bode J. (2006) The positive aspects of stress: strain initiates domain decondensation (SIDD). *Briefings in Functional Genomics and Proteomics.* 5(1), 24-31.

Wolfe J H, Fraser N W. (2008) Method of Delivering Genes to the Central Nervous System of a Mammal. U.S. Pat. No. 7,402,308 issued Jul. 22, 2008.

Zahn-Zabal M, et al. (2001) Development of stable cell lines for production or regulated expression using matrix attachment regions. *J. Biotechnol.* 87(1), 29-42.

Zhang J, et al. (2009) Transient expression and purification of chimeric heavy chain antibodies. *Protein Expr Purif.* 65(1), 77-82.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated polynucleotide comprising the nucleotide sequence as set forth in SEQ ID NO: 1.

2. An expression system for producing recombinant protein in a host cell comprising, operably linked: a gene for encoding a protein of interest; nucleotide sequences for operation of the expression system; and, an expression enhancer incorporated in cis in the expression system for enhancing expression of the gene, the expression enhancer being the polynucleotide of claim 1.

3. The expression system according to claim 2 being a plasmid vector.

4. The expression system according to claim 2 being an episomal vector.

5. The expression system according to claim 2, wherein the gene encodes a monoclonal antibody, an erythropoietin, an interferon, a vascular endothelial growth factor, a stem cell growth factor, a growth hormone or an insulin-like growth factor binding protein.

6. The expression system according to claim 2, wherein the nucleotide sequences for operation of the expression system comprise one or more of a promoter, an origin of replication, a leader, a splice donor, an intron, a splice accepter, a selectable marker, a cloning site, a restriction enzyme consensus site and a polyadenylation signal.

7. An isolated host cell comprising the expression system of claim 2.

8. The isolated host cell according to claim 7 which is a mammalian cell.

9. The host cell according to claim 8, wherein the mammalian cell is a Human Embryonic Kidney 293 (HEK293) cell, a Chinese Hamster Ovary (CHO) cell, a Baby Hamster Kidney (BHK21) cell, a PerC6 cell or a COS7 cell.

10. The host cell according to claim 8, wherein the mammalian cell is a Human Embryonic Kidney 293 (HEK293) cell or a Chinese Hamster Ovary (CHO) cell.

11. A method of producing a recombinant protein of interest comprising: transfecting a host cell with the expression system of claim 2; growing the host cell; expressing the gene to produce the protein of interest; and, recovering the protein of interest.

12. The method according to claim 11, wherein the host cell is a mammalian cell.

13. The method according to claim 11, wherein the host cell is a Human Embryonic Kidney 293 (HEK293) cell, a Chinese Hamster Ovary (CHO) cell, a Baby Hamster Kidney (BHK21) cell, a PerC6 cell or a COS7 cell.

14. The method according to claim 11, wherein the host cell is a Human Embryonic Kidney 293 (HEK293) cell or a Chinese Hamster Ovary (CHO) cell.

* * * * *